United States Patent [19]

Suzuki

[11] 4,254,104

[45] Mar. 3, 1981

[54] PROCESS FOR PREPARING STABLE OIL-IN-WATER EMULSIONS

[75] Inventor: Takashi Suzuki, Yokohama, Japan

[73] Assignee: Shiseido Co., Ltd., Tokyo, Japan

[21] Appl. No.: 631,250

[22] Filed: Nov. 12, 1975

[30] Foreign Application Priority Data

Nov. 12, 1974 [JP] Japan ................ 49-130336

[51] Int. Cl.³ .................... A61K 9/10; A61K 7/00
[52] U.S. Cl. .................... 424/170; 252/316; 424/47; 424/59; 424/70; 424/365
[58] Field of Search ............... 252/316; 424/170, 47, 424/365, 59, 70; 260/615 B

[56] References Cited

U.S. PATENT DOCUMENTS

| | | | |
|---|---|---|---|
| 2,593,112 | 4/1952 | Cross et al. ................ | 260/615 B |
| 2,677,700 | 5/1954 | Jackson et al. ............. | 260/615 B |
| 3,761,590 | 9/1973 | Fox ........................... | 424/170 X |
| 3,821,372 | 6/1974 | Vanlerberghe et al. ..... | 424/170 |
| 3,824,294 | 7/1974 | Kalopissis et al. .......... | 424/170 X |
| 3,839,212 | 10/1974 | McCoy ...................... | 260/615 B |
| 3,846,546 | 11/1974 | Lachampt et al. .......... | 424/170 |
| 3,876,760 | 4/1975 | Nersesian et al. .......... | 424/70 |

OTHER PUBLICATIONS

Balsam et al., Cosmetics: Science and Technology, Wiley–Interscience, New York, pp. 75–81, (1972).

*Primary Examiner*—Natalie Trousof
*Assistant Examiner*—Vera C. Clarke
*Attorney, Agent, or Firm*—Sughrue, Rothwell, Mion, Zinn and Macpeak

[57] ABSTRACT

A process for preparing a stable oil-in-water emulsion which comprises: adding a hydrophilic nonionic surface active agent to a water-soluble solvent; adding an oil phase thereto to form an emulsion of the oil phase in the water-soluble solution; and adding a water phase to the resulting emulsion. Cosmetics including such oil-in-water emulsions are also disclosed.

3 Claims, No Drawings

PROCESS FOR PREPARING STABLE OIL-IN-WATER EMULSIONS

BACKGROUND OF THE INVENTION

1. Field of the Invention

This invention relates to a process for preparing oil-in-water emulsions and cosmetics comprising such emulsions.

2. Description of the Prior Art

Emulsifying techniques are known for systems other than the oil-water system. For example, Petersen and Hamill conducted experiments on the emulsification of olive oil as a non-polar phase and glycerin, propylene glycol, or polyethylene glycol as a polar phase using various surface active agents. Furthermore, Petersen, Hamill and MacMahon emulsified glycerin and olive oil using a combination of a nonionic surface active agent and another surface active agent. The prior art, however, failed to provide emulsions having good stability. No consideration has ever been given to methods for preparing stable oil-in-water emulsions by adding water to an emulsion of oil in a water-soluble solvent.

Du Pont *Aerosol Guide Book*, 1969, contains some information on an emulsifying process in which a water-soluble solvent (propylene glycol) is added to a mixture of an oil and Freon gas. This report, however, does not relate to processes for preparing oil-in-water emulsions as in the present invention.

In the preparation of oil-in-water emulsions according to conventional techniques, the composition and the amount of a liquid phase are first determined, and then, the type and amount of emulsifier suitable therefor and the emulsifying method are chosen.

In selecting the emulsifier, the empirically established HLB values developed by Griffin et al have generally been utilized. This concept, however, essentially relates to the solubility of surface active agents in an oil-water system; generally, a surface active agent is dissolved in an oil phase or in an aqueous phase after its HLB has been adjusted to 7-18 in the case of an oil-in-water emulsion or to 3-7 in the case of a water-in-oil emulsion.

A special method is sometimes used in food engineering which comprises adding small amounts of an oil phase and an aqueous phase alternately to a surface active agent phase to form an emulsion.

In order to obtain a stable emulsion using a nonionic surface active agent, it is necessary to use a combination of a hydrophilic non-ionic surface active agent and an oleophilic nonionic surface active agent, and to orientate the surfactants at the interface of the oil and aqueous phases by increasing the area of the interface using a strong stirring means, e.g., a homogenizer. This requirement, however, is not the case when more than one kind of surfactant is used and large amounts of surfactants are used.

However, when the hydrophilicity of the hydrophilic nonionic surfactant is too high (e.g., an HLB of at least about 20), its surface activating ability is reduced, which makes it difficult to obtain a stable emulsion even when an oleophilic nonionic surfactant is used in combination therewith.

Generally, the stability of emulsions prepared by conventional emulsifying methods is not good at high temperatures because the non-ionic surfactants used have a relatively low cloud point. This problem is not generally encountered when ionic surfactants capable of providing electric charges on the interfacial membrane between the two phases are used. In such a case, emulsified oil droplets repel each another upon approaching because of the charging of the interface, and the coalescing or associating phenomenon seen in the case of using a nonionic surfactant scarcely occurs. Hence, an emulsion of good quality at high temperatures can be obtained. In order to obtain stable emulsions using nonionic surface active agents as are commercially available, it has been essential to use the same in combination with relatively large proportions of an ionic surface active agent.

SUMMARY OF THE INVENTION

We have performed extensive research on methods of preparing stable oil-in-water emulsions using nonionic surface active agents and, as a result, we succeeded in overcoming the difficulties encountered with conventional emulsifying methods using nonionic surfactants, and have provided a new process for preparing stable oil-in-water emulsions based on quite a different concept, which emulsions do not undergo coalescence even under severe conditions because the emulsified oil droplets are very small and uniform in size.

According to our invention, there is provided a process for preparing a stable oil-in-water emulsion which comprises; (a) dissolving a hydrophilic non-ionic surface active agent in a water-soluble solvent; (b) adding an oil phase to the thus formed solution form an emulsion of the oil phase in the water-soluble solvent; and (c) adding a water phase to the resulting emulsion to thereby form a stable water-in-oil emulsion.

In a highly preferred embodiment, the present invention relates to a process for preparing an emulsion which comprises adding a hydrophilic nonionic surface active agent comprising at least 15 moles of ethylene oxide to a water-soluble solvent to orientate the hydrophilic non-ionic surfactant at the interface of the two phases utilizing the low interfacial tension thereof, and then gradually adding a water phase to cause the water-soluble solvent to function as an aqueous phase in the resulting stable oil-in-water emulsion.

DETAILED DESCRIPTION OF THE INVENTION

As used herein, the term "oil" or "oil phase" is broadly used to describe an oil or an oil plus oil-soluble components desired in the final oil-in-water emulsion, e.g., oil-soluble antiseptics, active components and the like. Since oil-soluble components can be concentrated in the oil portion of the oil-in-water emulsion of the present invention, and such is desirable, it has been found easiest to introduce such components by dissolving them in the oil to be emulsified (oil phase).

Similarly, the term "water" or "water phase" is used in an analogous broad sense except, of course, the components optionally present therein are water soluble.

The process of this invention differs from conventional emulsifying methods. According to the present invention, a good emulsion of an oil phase and a water-soluble solvent is first prepared using a hydrophilic nonionic surfactant, and then a water phase is added to the emulsion to stabilize it. Since the water-soluble solvent has a much lower surface tension than water, the emulsification can be easily performed in the present invention without lowering interfacial tension.

Generally, a nonionic surface active agent containing an ethylene oxide chain becomes less irritating to the skin with longer ethylene oxide chain lengths, but, on the other hand, its surface activating ability lowers with longer ethylene oxide chain lengths. Accordingly, when a surface active agent having very high hydrophilicity is used, emulsification cannot be easily effected because the ability of such a surface active agent to reduce interfacial tension is low, and strong stirring is required. Even with strong stirring, the size of the droplets is difficult to reduce if the amount of surface active agent or the oil phase is small. This is the case even if the number of treating cycles is increased. However, when a hydrophilic nonionic surfactant is added to a water-soluble solvent such as propylene glycol, dipropylene glycol or 1,3-butyleneglycol, the dissolved state is quite different from the case of merely adding the hydrophilic nonionic surfactant to water. This is because a strong hydrogen bond which exists between water and a hydrophilic nonionic surfactant does not exist between a hydrophilic nonionic surfactant and a water-soluble solvent. Furthermore, such a surfactant, when in a water-soluble solvent, does not exhibit the same type of micelle formation as it does in water. It is believed that two or three molecules of the surfactant form a micelle, or the surfactant is dispersed in the form of single molecules.

According to the process of this invention, a hydrophilic nonionic surfactant is dissolved in a water-soluble solvent and an oil is added to the solution to form an emulsion. Since interfacial tension between the oil phase and the water-soluble solvent phase is low, a hydrophilic nonionic surfactant having low surface activating ability (the capability to impart an HLB (hydrophilic-lipophilic balance) of more than 20 but of not lowering surface tension to 40 dyne/cm or less) can be easily adsorbed onto the interface between the internal and external phases by the use of a very low stirring force. The subsequent addition of water to the resulting emulsion provides a stable emulsion with small droplets of uniform size.

Various factors influence the stability of emulsions. Generally, however, emulsions prepared using ionic surfactants having a charge have better stability. When a nonionic surfactant is used, only a weak charge can be expected, which is due to the difference in the dielectric constants of the oil phase, the aqueous phase, and the surfactant, unless a polar oil such as an ester oil is used. In addition, the charge of the interfacial membrane is also weak, and emulsions prepared using nonionic surfactants have inferior stability to those prepared using ionic surfactants.

Emulsions obtained by the process of this invention, on the other hand, are far more stable then those obtained using ionic surfactants in accordance with conventional methods. Various experimental results show that this seems to be due to the fact that in emulsions obtained by the process of this invention the interface is packed with closely spaced surfactant molecules, and the interfacial membrane acts like a solid film.

The size of the oil droplets obtained by the process of this invention is very small and the oil droplets are of a uniform size. Further, when external conditions are changed, the emulsions obtained by the process of this invention exhibit far better stability than emulsions obtained by conventional emulsifying methods. First, the emulsions are stable over a wide temperature range, and, especially, the stability is very good at high temperatures (for example, about 50°-90° C.). In particular, an emulsion of dimethyl polysiloxane (100 cps) has exceedingly good stability, and the oil droplets do not coalesce even upon boiling the emulsion. Thus, an emulsion of this type can be concentrated, if desired, by evaporating water therefrom.

With conventional emulsifying methods using nonionic surfactants, emulsification is difficult when the pH is highly acidic or highly alkaline (about pH 13). According to the emulsifying process of this invention, however, stable emulsions can be obtained under such conditions. In particular, there is a marked difference at highly acidic pH's (below pH 3), and emulsions of very good stability can be obtained even at such low pH's. Since the interfacial membrane of the oil droplets of an oil-in-water emulsion obtained by the process of this invention is extremely strong, coalescence of the droplets does not occur even when an aqueous solution of acetone, alcohol, ammonia or acetic acid (previously considered emulsion destroyers) are added to the continuous phase after emulsion preparation, i.e., the emulsion does not separate. Furthermore, the viscosity of an oil-in-water emulsion in accordance with this invention can be freely adjusted by adding further water. Also, since the difference in specific gravity between the continuous phase and the discontinuous phase can be freely controlled, it is possible to form a dilute emulsion, which has been difficult to do by conventional emulsifying methods.

Only one kind of hydrophilic nonionic surface active agent needs to be used in the process of this invention, and the amount thereof can be less than half that required in prior art emulsification processes. When a dilute emulsion is desired, the amount of the surfactant can be about one-tenth of that required in the prior art.

Nonionic surface active agents have lower skin irritation effects with longer ethylene oxide chains therein. All surfactants used in the present invention contain ethylene oxide in a relatively high molar amount, and the amount of surfactant can be very small as compared with the conventional methods. The value of oil-in-water emulsions prepared in accordance with this invention is thus very high in the cosmetic and pharmaceutical fields in view of their high safety to humans. If suitable water-soluble solvents and hydrophilic nonionic surfactants are selected, almost all oils as are used in the cosmetic and pharmaceutical field can be emulsified by the process of this invention.

Generally, suitable surfactants used to form stable emulsions by the process of this invention are those in which about 15 to about 120 moles of ethylene oxide or at least 15 moles of ethylene oxide plus about 1 to about 30 moles of propylene oxide are added to an oleophilic group containing about 8 to about 30 carbon atoms or those in which about 30 to about 100 moles of ethylene oxide is added to hydrogenated castor oil. Since these surfactants are all high molecular weight substances, attempts to utilize them directly in an oil-water system and to obtain a stable emulsion with a strong interfacial membrane have failed. However, by first adding the surfactant to a water-soluble solvent and then adding thereto an oil phase in accordance with this invention, the surfactant can be efficiently orientated at the interface. By adding water to the resulting system, a stable emulsion can be prepared.

The hydrophilic nonionic surfactants used in this invention can be classified into types I, II and III as described below in detail.

Type (I)

Compounds of the following formula

R—X—(CH$_2$CH$_2$O)$_n$H wherein R represents an alkane, alkene, aryl or cholestanol group containing at least 8 carbon atoms, X represents an ether (—O—) or ester (—COO—) group, and n represents an integer of 15 to 120. Of these compounds a polyoxyethylene (15–80 moles) lanolin alcohol ether, a polyoxyethylene (15–80 moles) lanolin fatty acid ester, a polyoxyethylene (15–60 moles) cholesteryl ether, and a polyoxyethylene (15–60 moles) cholestanyl ether are especially preferred.

Type (II)

Compounds of the formula $$R-X-(CH-CH_2O)_n-(CH_2CH_2O)_{n'}-H$$
$$\phantom{R-X-(}CH_3$$

wherein R represents an alkane, alkene, aryl or cholestanol group containing at least 8 carbon atoms, X represents an ether or ester group, n is an integer of 1 to 30, and n' is an integer of at least 15.

In the above formulae, preferred alkane and alkene groups have 8 to 30 carbon atoms and preferred aryl groups have the formula:

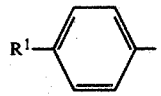

wherein R$^1$ is an alkane or alkene group of 2 to 24 carbon atoms.

Examples of preferred materials include

C$_{18}$H$_{37}$—O—(CH$_2$CH$_2$O)$_{30}$H and
C$_{17}$H$_{35}$COO—(CH$_2$CH$_2$O)$_{30}$H.

Of these compounds, adducts obtained by adding 20 to 80 moles of ethylene oxide to an adduct of cetanol, cholestanol or cholesterol and 1 to 12 moles of propylene oxide are most especially preferred.

Type (III)

Ethylene oxide adducts in which about 30 to about 100 moles of ethylene oxide is added to hydrogenated castor oil.

The process of this invention can be practiced using only one of the above-illustrated surfactants, but if desired two or more kinds can be used.

The water-soluble solvent used in the process of this invention serves to dissolve the hydrophilic nonionic surfactant and orientate the surfactant efficiently on the interface between the surfactant and the subsequently added oil phase. It can be chosen from a wide range of substances which are hydrophilic and can dissolve the surfactant, such as lower monohydric alcohols (having 1 to 7 carbon atoms), lower polyhydric alcohols (having 3 to 6 carbon atoms), polyethylene glycol (having a molecular weight of about 60 to about 2000), and lower aliphatic amines (having 2 or 3 carbon atoms).

Specific examples of the monohydric alcohols are methanol, ethanol, propanol, isopropanol, and benzyl alcohol. Specific examples of the polyhydric alcohols are glycerin, ethylene glycol, diethylene glycol, triethylene glycol, 2,5-hexanediol, 2,3-butylene glycol, 2,4-heptanediol, hexylylene glycol, 1,5-pentanediol, 1,4-butanediol, propylene glycol, 1,3-butylene glycol, polyethylene glycol, and dipropylene glycol. Specific examples of the amines are monoethanolamine, diethanolamine, and triethanolamine.

In the preparation of emulsions in accordance with this invention, one water-soluble solvent may be used or, if desired, the solubility of the surfactant can be conveniently varied by using a mixture of two or more water-soluble solvents.

Substantially all oils as are conventionally emulsified employed, ranging from non-polar oils to polar oils such as silicone oils, hydrocarbon oils, ester oils, etc., can be emulsified by the process of this invention.

Specific examples of the oil or oils which can be emulsified by the process of this invention include silicone oils such as dimethyl polysiloxane (100 cps), methylphenyl polysiloxane (20 cps), diphenyl polysiloxane (50 cps) or methyl hydrogen polysiloxane (100 cps); hydrocarbon oils such as liquid paraffin, squalane, terpene hydrocarbons and other synthetic hydrocarbon oils; and ester oils, for example, glycerin esters of straight-chain or branched-chain fatty acids such as glyceryl-triisostearate or glyceryl-tri-2-ethylhexanoate, branched alcohol esters of straight-chain or branched-chain fatty acids such as trimethylolpropane tri-2-ethylhexanoate or pentaerythritol tetra-2-ethylhexanoate, a 2-ethylhexylic acid ester of a glycerinsorbitan condensate or hexadecyl adipate and the like.

It has been confirmed that according to the process of this invention silicone oils or highly polar ester oils can be emulsified to provide a stable emulsion, while emulsions thereof are difficult to form from them by conventional emulsifying methods.

In an example of preparing an emulsion in accordance with the process of this invention from various oils using propylene glycol and a surfactant (an ethylene oxide adduct of hydrogenated castor oil), the number of moles of ethylene oxide (EO) in the surfactant per mole of hydrogenated castor oil which can gave the optimum results was determined, and the results are shown in Table 1 below.

TABLE 1

| Oils | Optimum number of moles of EO |
| --- | --- |
| Terpene hydrocarbon | 50 to 80 |
| Triglyceride of capric acid and lauric acid | 60 to 80 |
| Di-2-hexyl-decyl-adipate | 50 to 80 |
| Liquid paraffin (66 cps) | 40 to 80 |
| Dimethyl polysiloxane (100 cps) | 40 to 60 |
| Methylphenyl polysiloxane (20 cps) | 60 to 80 |
| Squalane | 40 to 80 |
| Liquid paraffin (22 cps) | 40 to 80 |
| Liquid paraffin (15 cps) | 40 to 80 |
| Olive oil | 40 to 80 |
| Pentaerythritol tetra-2-ethyl hexanate | 40 to 80 |

These results demonstrate that surfactants containing more moles of ethylene oxide are better for polar oils. Furthermore, since the average number of moles of ethylene oxide in the surfactant is higher than in conventional oil water systems and the range of the optimum number of moles of ethylene oxide to be added is wider, the choice of surface active agent(s) is quite simple. Further, it can be seen that there is an optimum number of moles of ethylene oxide according to the solubility of the surfactant in the water-soluble solvent and the oil.

Next, the lowest number of moles of ethylene oxide which provides stable oil-in-water emulsions using a specific oil and a specific water-soluble solvent was determined, and the results are shown in Table 2.

TABLE 2

| Type of oil | Type of solvent | | | | |
|---|---|---|---|---|---|
| | PG | DPG | 1.3BG | PEG-400 | PEG-1500 |
| Methyl phenyl polysiloxane (20 cps) | 50 | 60 | 70 | 60 | — | — |
| Dimethyl polysiloxane (100 cps) | 30 | 40 | 70 | 60 | — | — |
| Liquid paraffin (medium viscosity) (22 cps) | 30 | 40 | 30 | 60 | 60 | — |
| Di-2-hexyl-decyl adipate | 40 | 50 | 40 | 50 | 70 | — |
| Olive oil | 30 | 40 | 60 | 60 | 60 | — |
| Triglyceride of capric acid and lauric acid | 50 | 60 | 70 | 60 | — | 70 |
| Terpene hydrocarbon | 40 | 40 | 70 | 60 | 80 | 30 |
| Squalane | 30 | 30 | 30 | 40 | 60 | — |

Abbreviations
PG: propylene glycol
DPG: dipropylene glycol
1,3BG: 1,3-butylene glycol
PEG-400: polyethylene glycol-400 (molecular weight: 400)
PEG-1500: polyethylene glycol-1500 (molecular weight: about 920)
Gly: glycerine The results shown in Table 2 demonstrate that the lowest number of moles of ethylene oxide added which can form a stable oil-in-water emulsion differs according to the solubility of the surfactant (an adduct of hydrogenated castor oil and ethylene oxide) in the water-soluble solvent.

The oil-in-water emulsifier compositions obtained by the present invention may be used to prepare oil-in-water type cosmetic preparations, such as cleansing creams (or lotions), emollient creams (or lotions), hand creams (or lotions), suntan preparations, foundation make-up, eye make-up preparations, aerosol cosmetics, skin-covering cosmetics (beauty packs), stain removers, hair preparations and the like, without using other emulsifiers. In this case, the cosmetic creams, milky lotions or ointments may contain additives as are conventionally used for cosmetics or ointments, such as fatty materials, such as mineral oils, vaseline, squalane, beeswax, ceresine, etc.; solvents, such as propylene glycol, glycerin, etc.; powders, such as talc, etc.; antiseptics, such as alkyl-p-hydroxybenzoate, isopropylmethylphenol, etc.; perfumes; etc.; pigments; dyes; and the like, in conventional amounts.

The general method of preparing oil-in-water emulsions in accordance with the present invention is described below.

First, the hydrophilic nonionic surfactant is added to the water-soluble solvent and dissolved therein by heating the mixture at 50° to 75° C. The oil phase is then pre-heated to 50° to 75° C. and added to the solution with gradual stirring to form an emulsion of the oil in the water-soluble solvent. The emulsion is then diluted with the water phase, and, while stirring, cooled to 25° to 30° C. A stable oil-in-water emulsion is thus obtained.

In the first step of the process of this invention, the emulsion is prepared from about 1 to about 90 weight parts of the oil, about 1 to about 90 weight parts of the water-soluble solvent and about 0.2 to about 10 weight parts of the hydrophilic nonionic surfactant. In the second step, about 5 to about 95 weight parts of the emulsion of the oil in the water-soluble solvent emulsion is diluted with about 95 to about 5 weight parts of the water to form a stable oil-in-water emulsion.

According to conventional emulsifying methods, it has been difficult to prepare oil-in-water emulsions containing less than 10 parts, but at least 4 parts, of water. Such an emulsion which is highly stable can be prepared by the novel process of the present invention, with as little as about 4 parts of water.

The stability of an oil-in-water emulsion prepared by the process of this invention was compared with that of an emulsion prepared by a conventional emulsifying method, and the results are shown below.

| Test 1 | |
|---|---|
| Recipe of the sample:- | |
| Dimethyl polysiloxane | 28 parts |
| Propylene glycol | 20 parts |
| Polyoxyethylene (80 moles) glycerol tri-12-hydroxystearate ether | 2.0 parts |
| Deionized water | 50 parts |

Emulsifying Method I (Method of this Invention)

2.0 Parts of polyoxyethylene (80 moles) glycerol tri-12-hydroxystearate ether was added to 20.0 parts of propylene glycol, dissolved by heating at 50° C., and then allowed to cool to 25° C. 28.0 Parts of dimethyl polysiloxane (100 cps) was then added thereto to obtain a silicone/propylene glycol emulsion. The resulting emulsion was mixed using a homomixer. The resulting emulsion was diluted with 50 parts of deionized water at 25° C., and the mixture stirred to form an oil-in-water emulsion. The oil droplets in the emulsion had a particle size of 1 to 2 microns, and the size of the droplets was uniform.

Emulsifying Method II (Conventional Method)

20.0 Parts of propylene glycol and 2.0 parts of polyoxyethylene (80 moles) glycerol tri-12-hydroxystearate ether were dissolved in 50.0 parts deionized water, and the system heated to 70° C. Then, 28.0 parts of dimethylpolysiloxane (100 cps) was added to the solution at 70° C. and the system emulsified using a homomixer to form an oil-in-water emulsion followed by cooling to 25° C. The oil droplets in the emulsion had a particle size of 2 to 15 microns.

Each of the emulsions obtained above was placed in a graduated test tube, and permitted to stand at varying temperatures for various times. The stability of the emulsions was evaluated on a scale of 0 to 10, in which 10 shows that the oil phase separated completely (separation into two phases), and 0 shows that no separation occurred. The emulsions were observed after 1, 7 and 30 days from the times of preparation of the emulsions. The results obtained are shown in Table 3.

TABLE 3

| Temperature (°C.) | 0 | | | Room Temperature (at 25° C.) | | | 37 | | | 50 | | |
|---|---|---|---|---|---|---|---|---|---|---|---|---|
| Emulsifying method | Number of days that passed | | | | | | | | | | | |
| | 1 | 7 | 30 | 1 | 7 | 30 | 1 | 7 | 30 | 1 | 7 | 30 |
| Method I | 0 | 0 | 0 | 0 | 0 | 0.1 | 0 | 0 | 0.1 | 0 | 0.1 | 0.1 |
| Method II | 0.1 | 0.2 | 10 | 0.2 | 10 | 10 | 10 | 10 | 10 | 10 | 10 | 10 |

As is shown in Table 3, there is a clear difference in stability between the emulsions prepared by methods I and II.

The oil droplets in the emulsion prepared by method II had a large particle size, i.e., 2 to 15 microns, and the emulsion separated into two phases after 7 days at 37° and 50° C. Further, droplet coalescence was observed. In the emulsion prepared by method I, phase separation was observed somewhat at the bottom of the test tube at 37° and 50° C., but no coalescence of the oil droplets was observed.

Thus, according to the process of this invention, dimethyl polysiloxane which could not be emulsified by conventional methods (even with the aid of a hydrophilic nonionic surfactant) can be formed in a very stable emulsion. In fact, coalescence of the droplets does not occur even when the emulsion is boiled, and it is even possible to concentrate the emulsion.

Test 2

To the emulsion prepared by the process of this invention there was added an amount of an alcohol heretofore known as an emulsion destroyer, and the stability of the emulsion examined.

Preparation of Samples 0.5 Parts of polyoxyethylene (80 moles) glycerol tri-12-hydroxystearate ether was added to 4.0 parts of propylene glycol, dissolved by heating at 50° C., and then allowed to cool to 25° C. Then 5.0 parts of dimethyl polysiloxane (100 cps) was added thereto at 25° C. The resulting mixture was then mixed using a homomixer. To the resulting emulsion there was added 40.5 parts of deionized water with stirring at 25° C. to form an oil-in-water emulsion. Then, 50.0 parts of ethanol was further added thereto and the mixture stirred.

The resulting emulsion was placed in a graduated test tube and allowed to stand at 37° and 50° C. for an extended period of time to examine its stability. It was found that most of the droplets in the emulsion had a particle size of less than 1 micron, and the interfacial membrane was tough. The results also showed that even when the emulsion was stored in a sealed container for over one year in a constant temperature vessel at 37° C. or 50° C. after the addition of the alcohol, no coalescence of the droplets occurred.

For comparison, the same amount of ethanol was added to an emulsion of the same composition prepared by the conventional method earlier described. When the emulsion was allowed to stand for one day at 37° C., separation began to occur, and after one month complete separation occurred.

With respect to an emusified composition containing a large quantity (20 to 80 parts) of an alcohol, Japanese Patent Publication No. 16955/67 discloses a method which comprises dissolving a surface active agent of the phosphate ester type into an alcohol phase, adding an oil to the solution to dissolve or emulsify the oil therein, and then adding water. This method, however, is quite different in emulsifying mechanism from the emulsifying process of this invention. In the emulsifying method disclosed in Japanese Patent Publication No. 16955/67, a phosphate ester surfactant (a type of anionic surfactant) and an oil are dissolved or emulsified in an alcohol phase. While a part of the oil is emulsified, most of the oil forms a solution of three components (the alcohol, the surfactant, and the oil). The orientation of the surfactant is not so important.

Accordingly, when it is desired to emulsify a non-polar oil by the above process, it is necessary to add another surfactant which is highly miscible with the alcohol. The addition of a large amount (more than the amount of the alcohol) of non-polar oil is difficult. Dimethyl polysiloxane (100 cps), for example, cannot be formed into a stable emulsion by such a method.

The emulsifying process provided by the present invention is quite new and permits the elimination of the various defects of conventional emulsifying methods. According to the process of this invention, almost all oils ranging from the most difficult to emulsify silicone oils to the polar oils can be emulsified easily with mild stirring using only one hydrophilic nonionic surfactant having a low interfacial tension-reducing ability in a small amount. The process of this invention is quite different from the conventional techniques based on the concept of HLB.

Since the interfacial membrane of the emulsions obtained by the process of this invention is very strong, no coalescence of oil droplets occurs. Thus, even after preparation of the emulsion, one can add water or a water-soluble solvent to the continuous phase (aqueous phase). This makes it possible to produce emulsions suitable for a variety of applications. Furthermore, emulsions in accordance with this invention have good stability at high temperatures (50° to 100° C.), and do not undergo phase separation over a long period of time. If desired, such emulsions can even be concentrated by heating. Thus, according to the present invention, stable emulsified compositions surpassing conventional emulsions can be obtained.

The following Examples illustrate the present invention in greater detail without limiting the same. All examples were conducted at atmospheric pressure and at room temperature (about 25° C.), unless otherwise indicated.

EXAMPLE 1

2.0 Parts of polyoxyethylene (40 moles).polyoxypropylene (12 moles) cetylalcohol ether was dissolved in a mixture of 5.0 parts of polyoxyethylene glycol-200 (molecular weight: 200) and 5.0 parts of dipropylene glycol at 50° C. and the system allowed to cool to 30° C. 75.0 Parts of dimethylpolysiloxane (100 cps) was then gradually added to the resulting solution while stirring at 30° C. to prepare a semi-transparent emulsion of the dimethyl polysiloxane in the water-soluble solvent. When 13.0 parts of deionized water was further added thereto at 30° C., a stable dimethyl polysiloxane emulsion containing dimethyl polysiloxane droplets of a small size (less than 1 micron) was obtained. When water or another water-soluble solvent was further added to the emulsion, no coalescence of the oil droplets occurred. Thus, this emulsion can be utilized for cosmetics, pharmaceuticals and aqueous-based paints, if desired.

EXAMPLE 2

2.0 Parts of polyoxyethylene (30 moles) lanolin alcohol ether and 1.0 part of polyoxyethylene (20 moles)-polyoxypropylene (12 moles) cetyl alcohol ether were dissolved in 7.0 parts of propylene glycol by heating at 50° C. 2.0 Parts of squalan, 4.0 parts of deodorized lanolin, 10.0 parts of purified Vaseline, 2.0 parts of beeswax, 24.0 parts of di-2-hexyl-decyl adipate and 0.3 parts of methyl-p-hydroxybenzoate were dissolved by heating at 70° C., allowed to cool to 50° C., whereupon 0.5 parts of perfume and 0.2 parts of dl-α-tocopheryl palmitate were added thereto, whereafter the system was gradually added to the above-formed propylene glycol phase with stirring at 50° C. to yield an almost semi-transparent oil/propylene glycol emulsion. When deionized water was further added to the emulsion at 25° C., a stable oil-in-water emulsion was obtained. The emulsion could be used as a skin-nourishing cream, if desired. Upon dilution with water, a skin-nourishing lotion was produced.

EXAMPLE 3

1.5 Parts of polyoxyethylene (50 moles) glycerol tri-12-hydroxystearate ether was dissolved in 5.0 parts of propylene glycol at 50° C. and the system allowed to cool to 30° C. 0.7 part of perfume and 0.2 part of methyl-p-hydroxybenzoate were dissolved in 20.0 parts of glyceryl tri-2-ethylhexanate and 20.0 parts of dimethyl-polysiloxane (100 cps) at 50° C., and the solution then allowed to cool to 30° C. The resulting solution was gradually added to the above formed propylene glycol phase with stirring to yield an oil/propylene glycol emulsion. 54.0 parts of deionized water was added to the emulsion at 25° C. and 10.0 parts of Freon gas (sold under the name 12/114=6/4; a product of E. I. du Pont de Nemours & Co., Inc.) injected into the emulsion under pressure. A stable, aqueous Freon emulsion was obtained which could be utilized in an aerosol product.

EXAMPLE 4

2.0 Parts of polyoxyethylene (100 moles) glycerol tri-12-hydroxy stearate ether was dissolved in 5.0 parts of ethyl alcohol (99% by weight percent) with stirring at 25° C., and then 5.0 part of ammonia water (28.0% by weight percent) added thereto at 25° C. Then, 35.0 parts of squalan and 20.0 parts of di-2-hexyl decyl adipate were gradually added thereto with stirring at 25° C. to form an oil/ammonia+alcohol emulsion. Further, 33.0 parts deionized water was added to form a stable ammonia-containing cream which could be used as a medicinal cream to relieve the itching of insect bites, for example.

EXAMPLE 5

0.2 Part of polyoxyethylene (30 moles).polyoxypropylene (1 mole) dihydrocholesteryl ether was dissolved in 4.0 parts of 1.3-butylene glycol by heating to at 50° C., and the system allowed to cool to 25° C. 0.05 part of perfume, 0.2 part of dl-α-tocopherylpalmitate and 0.1 part of methyl-p-hydroxybenzoate were dissolved in 6.0 parts of pentaerythritol tetra-2-ethylhexanate by heating at 50° C., and the solution allowed to cool to 25° C. The resulting solution was added to the above formed 1,3-butylene glycol phase, and mixed in a homomixer. There was thus obtained an oil/1,3-butyl glycol emulsion. 79.8 parts of deionized water was added thereto, and then 10.0 parts ethyl alcohol (99% by weight percent) added thereto. A stable, dilute emulsion was formed (oil droplet size less than 1 micron). This product showed characteristics intermediate a conventional toilet water and a milky lotion, and exhibited moderate oiliness and a refreshing feel. Since the amount of the surfactant used was small, the emulsion did not become sticky and could be favorably used as a cosmetic from the viewpoint of skin safety.

EXAMPLE 6

2.0 Parts of polyethylene glycol-1500 (m.W.=920), 3.0 parts of polyoxyethylene glycol-6000 and 15.0 parts of titanium dioxide were added to 35.0 parts of deionized water. The mixture was stirred and 10.0 parts of a vinyl acetate emulsion and 8.0 parts of polyvinyl alcohol having a molecular weight of 88,000 wetted with 10.0 parts ethyl alcohol (about a 44 weight percent ethyl alcohol solution) added thereto. The mixture was heated to about 50° C. and stirred (PVA phase). 0.2 Part of polyoxyethylene (60 moles) glycerol tri-12-hydroxystearate ether was dissolved in 5.0 parts of propylene glycol at 50° C. (PG phase) and separately 0.2 part of dl-α-tocopheryl palmitate, 0.3 part of methyl-p-hydroxybenzoate and 0.5 part of perfume were added to 2.0 parts of squalan and 5.0 parts of glyceryl tri-2-ethylhexanate, whereafter the system was dissolved at 50° C. and then added to the PG phase with stirring, whereafter 4.0 parts of deionized water was added to stabilize the resulting emulsion. The resulting stable emulsion was then added to the PVA phase with stirring to uniformly mix, followed by permitting the system to cool to 25° C. There was thus obtained a skin-covering cosmetic (make-up-pack) in which the powder and oil were present in a stable manner.

EXAMPLE 7

2.0 Parts of polyoxyethylene (50 moles) glycerol tri-12-hydroxy stearate ether was dissolved in 5.0 parts of benzyl alcohol at 50° C., and an oil phase consisting of 10 parts of liquid paraffin (15 cps), 5.0 parts of Vaseline, 0.2 part of methyl-p-hydroxybenzoate and 0.5 part of perfume was added to the benzyl alcohol solution while stirring to emulsify the system at 50° C. Then, 2.0 parts of deionized water was added to stabilize the emulsion. The concentrated emulsion obtained was added, with stirring, to 0.5 part of a carboxy vinyl polymer aqueous solution phase (Carbopol 94; a product of the B. F. Goodrich Chemical Co.) containing 20 parts of dipropylene glycol and 2.0 parts of triethanolamine, and the system uniformly mixed followed by cooling to 25° C. A lotion-like stain remover for hair dyes (viscosity 4,000 cps) which was stable with the passage time and which contained uniform oil droplets and had excellent skin-safety was obtained.

EXAMPLE 8

3.0 Parts of polyoxyethylene (40 moles) β-cholesteryl ether was dissolved in 10 parts of benzyl alcohol at 50° C. (BA phase). Then, an oil phase consisting of 18.0 parts squalene, 5.0 parts of olive oil, 0.3 part of methyl-p-hydroxybenzoate and 0.5 part of perfume was heated to 50° C. and added to the BA phase while stirring. 1.0 part of deionized water was then added to the system and the mixture stirred to stabilize the emulsion and form a concentrated emulsion. 1.5 parts of xanthene gum which was wetted with 25.0 parts of dipropylene glycol, 4.0 parts of triethanolamine and 36.5 parts deionized water were added thereto and the system uniformly mixed at 50° C. (aqueous phase). The resulting aqueous phase was added with stirring to the earlier obtained concentrated emulsion while maintaining the system at 50° C. and thereafter cooling to 30° C. A stain remover for hair dyes of excellent strength was obtained.

EXAMPLE 9

0.5 Part of polyoxyethylene (40 moles) lanolin alcohol ether was dissolved in 3.0 parts of benzyl alcohol by heating at 50° C. An oil phase consisting of 7.0 parts of liquid paraffin (15 cps), 3.0 parts of glyceryl triisostearate, 0.2 part of methyl-p-hydroxybenzoate, and 0.3 parts of perfume was added to the benzyl alcohol phase while stirring at 50° C. With continued stirring, 1.5 parts of deionized water was further added to stabilize the emulsion and thus form a concentrated emulsion. An aqueous phase was then prepared by mixing 20.0 parts propylene glycol, 1.5 parts of triethanolamine, 1.0 part of hydroxymethyl cellulose and 62.5 parts of deionized water at 30° C., and the aqueous phase added with stirring to the concentrated emulsion. A stain remover for hair dyes was thus prepared.

While the invention has been described in detail and with reference to specific embodiments thereof, it will be apparent to one skilled in the art that various changes and modifications can be made therein without departing from the spirit and scope thereof.

What is claimed is:

1. A process for preparing a stable oil-in-water emulsion which comprises:

adding about 0.2 to about 10 weight parts of a hydrophilic nonionic surface active agent selected from the group consisting of (1) a compound of the formula

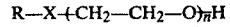

wherein R represents an alkane, alkene, aryl or chloestanol group containing 8 to 30 carbon atoms, X represents an ether or ester group, and n represents an integer of 15 to 120, (2) a compound of the formula

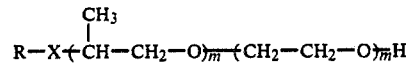

wherein R and X are the same as defined above, and m and m' represent an integer of 1 to 30 and at least 15, respectively, and (3) an ethylene oxide adduct in which about 30 to about 100 moles of ethylene oxide is added to hydrogenated castor oil, to about 1 to about 90 weight parts of a water-soluble solvent capable of dissolving said surface active agent selected from the group consisting of (1) a lower monohydric alcohol having 1 to 7 carbon atoms, (2) a lower polyhydric alcohol having 3 to 6 carbon atoms, (3) polyethylene glycol having a molecular weight of about 60 to about 2000, and (4) a lower aliphatic amine having 2 or 3 carbon atoms;

adding about 1 to about 90 weight parts of an oil thereto to form an emulsion of the oil in the water-soluble solvent; and adding about 5 to about 95 weight parts of water to the resulting emulsion.

2. A process of claim 1, wherein said hydrophilic nonionic surface active agent is selected from the group consisting of polyoxyethylene (15-80 moles ethylene oxide) lanolin alcohol ether, polyoxyethylene (15-80 moles ethylene oxide) lanolin fatty acid ester, polyoxyethylene (15-60 moles ethylene oxide) cholesteryl ether, polyoxyethylene (15-60 moles ethylene oxide) cholestanyl ether, polyoxyethylene (20-80 moles ethylene oxide) polyoxypropylene (1-12 moles propylene oxide) cetanol ether, polyoxyethylene (20-80 moles ethylene oxide) polyoxypropylene (1-12 moles propylene oxide) cholestanyl ether, polyoxyethylene (20-80 moles ethylene oxide) polyoxypropylene (1-12 moles propylene oxide) cholesteryl ether, and polyoxyethylene (30-80 moles ethylene oxide) glycerol tri-12-hydroxystearate ether.

3. A process of claim 1, wherein said water-soluble solvent is selected from the group consisting of methanol, ethanol, propanol, isopropanol, benzyl alcohol, glycerin, ethylene glycol, diethylene glycol, triethylene glycol, 2,5-hexanediol, 2,3-butylene glycol, 2,4-heptanediol, hexylylene glycol, 1,5-pentanediol, 1,4-butanediol, propylene glycol, 1,3-butylene glycol, dipropylene glycol, monoethanolamine, di-ethanolamine, and triethanolamine.

* * * * *